United States Patent [19]

Brewer

[11] Patent Number: 5,172,810

[45] Date of Patent: Dec. 22, 1992

[54] RECEPTACLE FOR HOLDING DENTAL BURRS

[76] Inventor: Charles A. Brewer, 105 Via Wazier, Newport Beach, Calif. 92660

[21] Appl. No.: 788,342

[22] Filed: Nov. 6, 1991

[51] Int. Cl.⁵ ............................................ B65D 83/10
[52] U.S. Cl. .................................. 206/369; 206/45.15;
 206/45.19; 206/368; 206/63.5; 433/77; 422/300
[58] Field of Search ...................... 206/63.5, 368, 369,
 206/379, 425, 439, 45.15, 45.18, 45.19; 433/77,
 79, 165; 422/300

[56] References Cited

U.S. PATENT DOCUMENTS

| | | | |
|---|---|---|---|
| 1,684,417 | 9/1928 | Silberman | 206/63.5 |
| 3,092,443 | 6/1963 | Dietz | 206/63.5 |
| 3,248,167 | 4/1966 | Friedman | 206/369 |
| 3,583,556 | 6/1971 | Wagner | 206/45.18 |
| 3,890,096 | 6/1975 | Nichol et al. | 206/63.5 |
| 4,006,821 | 2/1977 | Sautter | 206/45.15 |
| 4,050,894 | 9/1977 | Genis | 206/368 |
| 4,253,830 | 3/1981 | Kazen et al. | 206/379 |
| 4,660,719 | 4/1987 | Peterson et al. | 206/45.15 |
| 4,867,305 | 9/1989 | Schneider | 206/63.5 |
| 4,930,660 | 6/1990 | Porteous | 220/63.5 |
| 4,959,199 | 9/1990 | Brewer | 422/300 |
| 5,006,066 | 4/1991 | Rouse | 206/379 |
| 5,071,346 | 12/1991 | Domaas | 206/379 |

FOREIGN PATENT DOCUMENTS 304543 3/1955 Switzerland ........................ 206/63.5

*Primary Examiner*—David T. Fidei
*Attorney, Agent, or Firm*—Gordon L. Peterson

[57] ABSTRACT

A receptacle for holding dental burrs comprising a container which includes a container body and a cover. The container body provides a compartment having an open end. At least one dental burr holder is provided in the compartment with the dental burr holder having a plurality of bores terminating in an opening. The dental burr holders are pivotally attached to the container body for pivotal movement between a first position in which the opening of the bores face generally outwardly of the open end of the compartment and a second position in which the openings of the bores are closer to a bottom wall of the container body than in the first position. The container has at least one aperture for providing fluid access to the compartment.

18 Claims, 2 Drawing Sheets

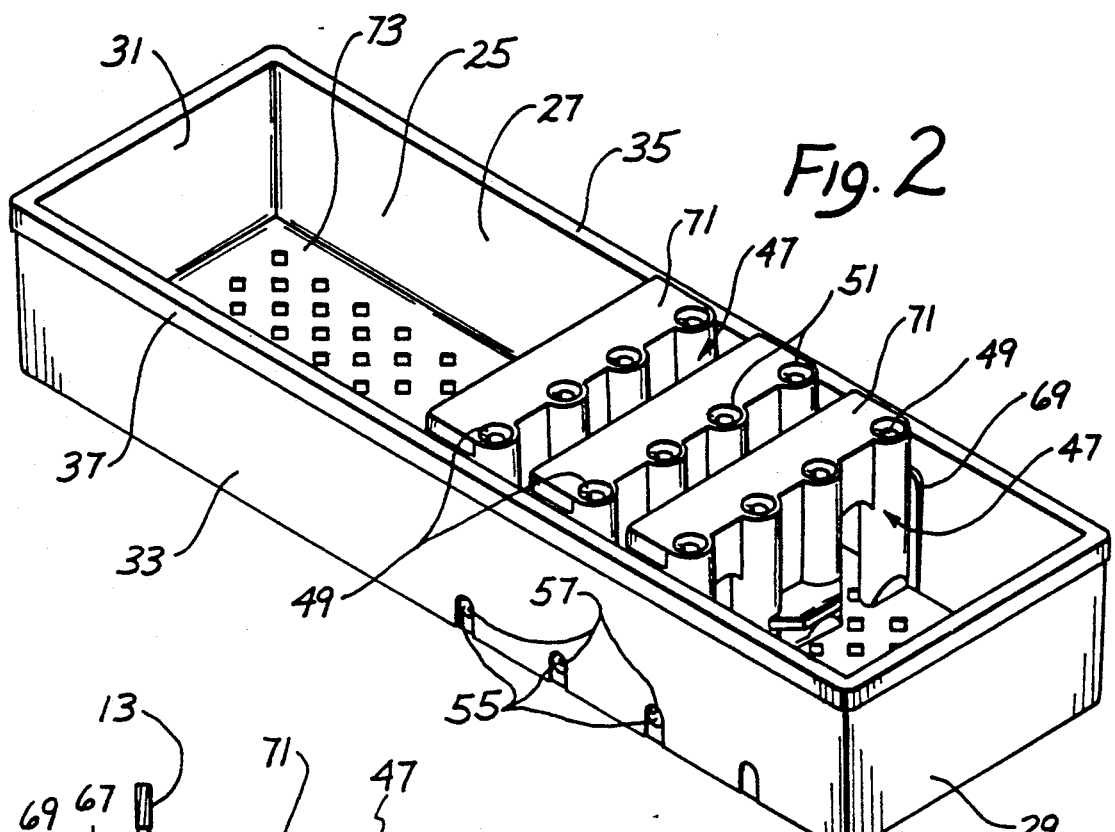
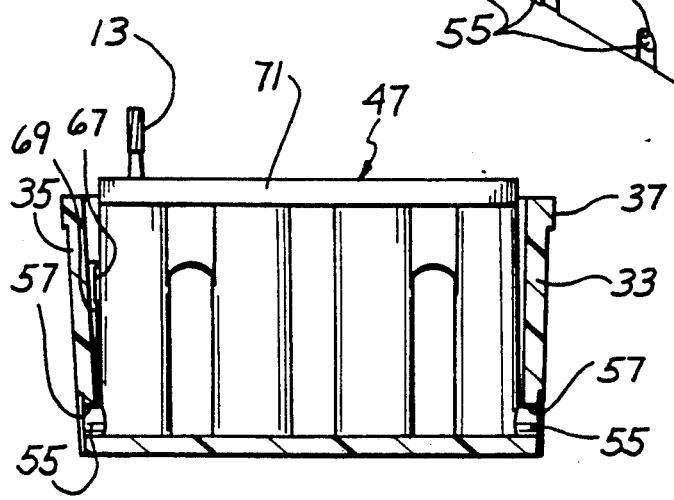
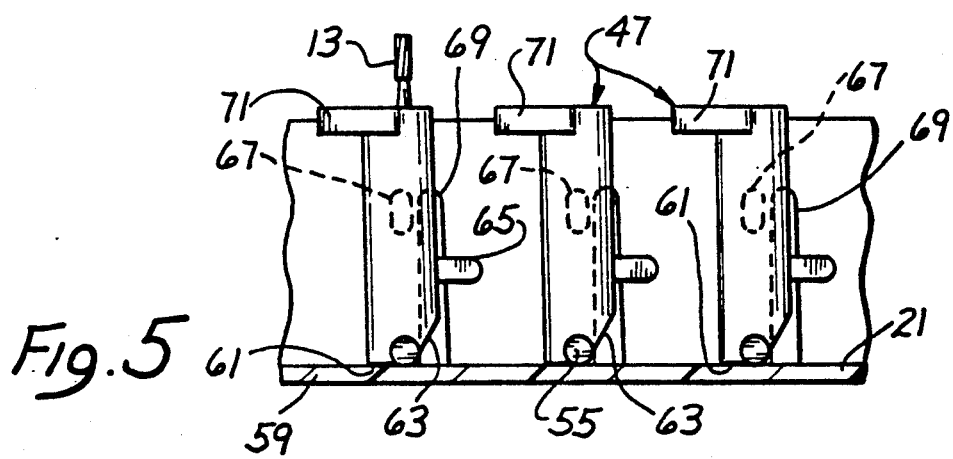

RECEPTACLE FOR HOLDING DENTAL BURRS

BACKGROUND OF THE INVENTION

This invention relates to a receptacle for holding small elongated objects, such as dental burrs.

Dental burrs are short, small diameter members which come in assorted lengths and configurations. For example, dental burrs may range in length from about 0.625 inch to about 1.062 inch and may have a diameter of about 0.093 inch or about 0.062 inch.

In the course of his work, a dentist commonly has need for various sizes and configurations of dental burrs, and so it is desirable to have these small members, which are difficult to manually manipulate, held for convenient grasping. It is also desirable to have a place to store used dental burrs where they will not get lost and contaminate the unused sterile dental burrs.

Perhaps the most important need is to provide for the cleaning and sterilization of used dental burrs so they can be reused. This process can be facilitated by the batch handling, cleaning and sterilization of an assortment of dental burrs.

SUMMARY OF THE INVENTION

This invention provides a receptacle for holding dental burrs. The receptacle is adapted to hold an assortment of dental burrs in a way to facilitate manual grasping of the burrs. In addition, the receptacle holds the burrs to facilitate cleaning and sterilizing of the burrs. An optional, but desirable, feature of the invention is to provide within the receptacle a region of space for collecting used, non-sterile burrs and retaining them to minimize risk of loss and prevent them from contacting the sterile burrs.

A receptacle constructed in accordance with the teachings of this invention comprises a container, including a container body and a cover. The container body includes a transverse wall and a peripheral wall joined to the transverse wall to define a compartment having an open end. The cover is positionable over the open end of the compartment. With this construction, each of the transverse wall and cover have an outer surface, and the distance between these outer surfaces with the cover positioned over the open end of the compartment is no greater than about 0.810 inch.

At least one dental burr holder is provided in the compartment. The dental burr holder has a plurality of bores with each of the bores terminating in an opening. Each of the bores is sized and adapted to receive a dental burr through its opening. The dental burr holder holds the dental burrs, with a portion of the dental burr projecting beyond the holder to facilitate manual grasping of the burrs.

With the dental burr holder in an upright position and the dental burrs projecting from them a sufficient distance to be easily grasped, the overall height of the receptacle would be too great to fit within existing dental instrument cassettes which are used in the cleaning and sterilizing process. In order to enable the receptacle to have a small enough vertical dimension to fit within existing cassettes, this invention provides for the pivotal attachment of the dental burr holder to the container body. With this arrangement, the dental burr holder is pivotable between a first position in which the openings of the bores of the dental burr holder face generally outwardly of the open end of the compartment to facilitate access to any dental burrs in the bores and a second position in which the openings of the bores are closer to the transverse wall than in the first position. Thus, in the second position, the dental burr holder is pivoted so that the overall height of the receptacle can fit within the desired cassette. Also, with this arrangement, the dental burr holder may project through the open end of the compartment and out of the compartment in the first position and lie entirely within the compartment in the second position.

So that cleaning and sterilizing fluids, which are typically solutions, can contact the dental burrs in the receptacle, the container has aperture means which provides access to the compartment. Although the aperture means could be a single large aperture, preferably it includes a plurality of apertures which are sufficiently small to prevent the passage of a dental burr having a diameter of about 0.062 inch through the apertures. One preferred location for the apertures is in the transverse wall and the cover. To enhance contact between the cleaning and/or sterilization solution and the dental burrs, the bores preferably extend all the way through the dental burr holder.

Any desired number of the dental burr holders may be employed in the compartment, and preferably, a plurality of dental burr holders are pivotally attached to the peripheral wall of the container body. This increases the number of burrs that can be held within the compartment. Preferably, each of the dental burr holders is separately pivotable between the first and second positions. Also, the dental burr holders are preferably arranged in generally parallel relationship.

In the second position, the receptacle is used as a container for dental burrs during cleaning and sterilization. It is desirable that the dental burrs be retained individually within an associated bore of the dental burr holder during this time. Although this can be accomplished in different ways, preferably means is provided on one dental burr holder which is cooperable with the cover for holding dental burrs in the bores of an adjacent dental burr holder when the latter dental burr holder is in the second position. Although this means may take various different forms, in a preferred construction, it includes a flange on the dental burr holder.

Means is provided to retain the dental burr holder in the first and second positions. Although such means can take many different forms, in a preferred construction, it includes means cooperating with the transverse wall to define the second position. For example, this means may include a tab on the dental burr holder which contacts the transverse wall in the second position. Cooperating flat surfaces on the dental burr holder and the transverse wall can be used in association with the pivotal attaching means to restrain or prevent pivoting of the dental burr holder out of the first position in the wrong direction.

The cover may be permanently attached to the container body as by a hinge for movement to cover and uncover the open end of the compartment. However, preferably the cover is a separate member which can be removably affixed to the container body to close the open end of the compartment.

A space is preferably provided in the receptacle for holding used dental burrs. This may be provided, for example, by spacing the dental burr holders from a region of the peripheral wall. For example, the peripheral wall may include an end wall, and the space can be provided between the end wall and the adjacent dental burr holder.

The method of this invention includes inserting dental burrs into the bores of the dental burr holder with the dental burr holder being in the first position and then pivoting the dental burr holder to the second position. The cover is then placed on the container body, and the receptacle with the dental burrs therein is subjected to a cleaning or sterilizing fluid to clean or sterilize the dental burrs.

The invention, together with additional features and advantages thereof may best be understood by reference to the following description taken in connection with the accompanying illustrative drawings.

BRIEF DESCRIPTION OF THE DRAWINGS

FIG. 2 is a perspective view similar to FIG. 1 with the cover removed and with the dental burr holders in the first position.

FIG. 4 is a transverse sectional view through the receptacle with a dental burr in one of the bores.

FIG. 5 is a fragmentary, side elevational view showing the dental burr holders in the first position, the container body in section and a dental burr in one of the bores.

DESCRIPTION OF THE PREFERRED EMBODIMENT

Figure 1:
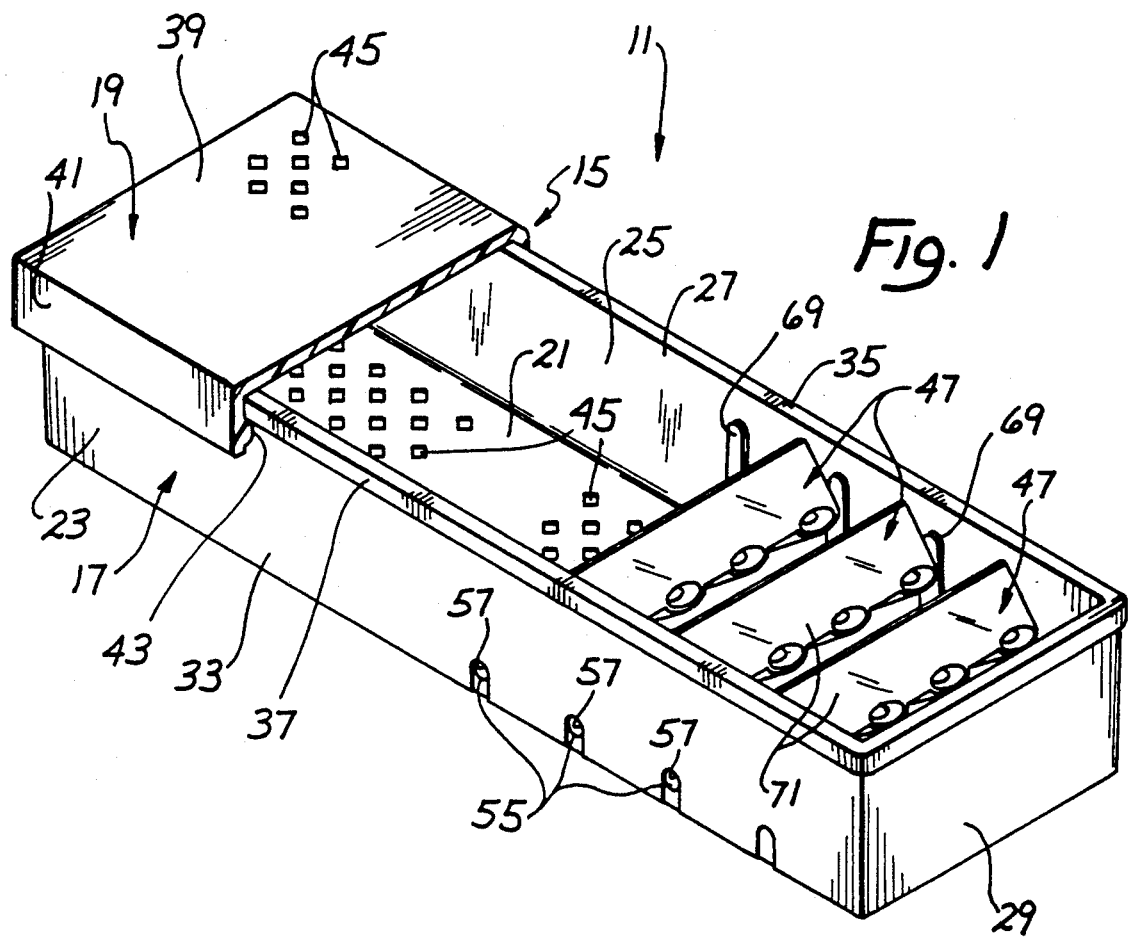
FIG. 1 is a perspective view of a receptacle for holding dental burrs with the cover broken away to expose the interior or the receptacle and with the dental burr holders in the second position.
Figure 3:
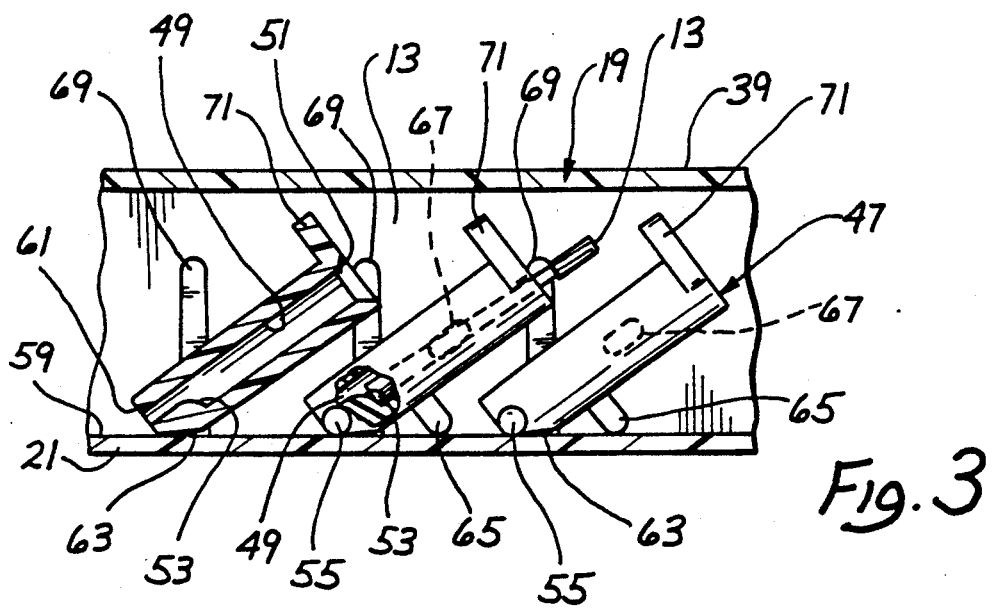
FIG. 3 is a fragmentary, sectional view taken longitudinally of the receptacle with one of the dental burr holders being shown in elevation and another of the dental burr holders partially in section with a dental burr in one of the bores.

FIG. 1 shows a receptacle 11 adapted to hold dental burrs 13 (FIGS. 3-5). The receptacle 11 comprises a container 15 which includes a container body 17 and a cover 19. The container body 17 includes a transverse wall which, in the embodiment illustrated, is a bottom wall 21 and a peripheral wall 23 which cooperate to define a compartment 25 having an open end 27 opposite the bottom wall 21.

Although many different constructions can be employed, in the illustrated embodiment, the container 15 is elongated, and the peripheral wall 23 has opposite end walls 29 and 31 (FIG. 2) and opposite side walls 33 and 35 which are much longer than the end walls. The upper end of the peripheral wall is thickened to form an elongated, continuous rib 37 which extends for the full length of the peripheral wall. The container body 17 and the cover 19 are separately molded from a suitable polymeric material, such as polyethersulfone.

The cover 19 has a transverse wall in the form of a top wall 39 and a peripheral wall 41, with an integral, continuous inwardly directed bead 43 which cooperates with the rib 37 to removably attach the cover to the container body 17. As shown, the vertical dimension (as viewed in FIG. 1) of the peripheral wall 41 is much less than the vertical dimension of the peripheral wall 23. The cover 19, when attached to the container body 17, closes the open end 27. However, the container 15 has apertures 45 which provide access to the compartment 25 even when the cover 19 is mounted on the container body 17. In this embodiment, the apertures 45 are provided in the bottom wall 21 and the top wall 39. The apertures 45 are sufficiently small to prevent the passage of any of the dental burrs 13, even those having a diameter as low as about 0.062.

A plurality of identical dental burr holders 47 (three being illustrated) are provided in the compartment 25. Each of the dental burr holders may be separately molded from a suitable polymeric material, such as polyethersulfone. As shown in FIG. 1, each of the dental burr holders has a plurality of bores 49 (four being illustrated), with each of the bores terminating in a radially, outwardly flared opening 51. Each of the bores 49 is sized and adapted to receive one of the dental burrs 13 through its opening 51. The bores 49 extend all the way through the dental burr holder 47, and the end of the bore 49 near the bottom wall 21 is of restricted cross-section to provide a shoulder 53 (FIG. 3) to support the dental burr 13. The location of the shoulder 53 within the bore 49 determines the length of dental burr 13 that the bore is adapted to retain. For example, by providing one of the bores 49 with the shoulder 53 farther away from the bottom wall 21, that bore is adapted to receive a shorter dental burr.

The dental burr holders 47 are mounted in generally parallel relationship in the compartment 25 for pivotal movement between an upright or first position (FIGS. 2, 4 and 5) and a downward or second position shown in FIGS. 1 and 3. In the upright position, the openings 51 of the bores 49 face generally outwardly of the open end 27 of the compartment 25 to facilitate access to the burrs 13 in the bores as shown in FIGS. 2, 4 and 5. More specifically, in the embodiment illustrated, the axes of the bores 49 are essentially perpendicular to the bottom wall 21 in the upright position. In addition, the dental burr holders 47 project through the open end 27 and out of the compartment 25 in the upright position as shown in FIGS. 2, 4 and 5. The length that the burrs 13 project above the associated dental burr holders 47 prevents the cover 19 from being attached onto the container body 17 using the rib 37 and the bead 43 when the dental burr holders 47 are in the upright position.

In the down position of FIGS. 1 and 3, the openings 51 of the bores 49 are closer to the bottom wall 21 than in the upright position. Specifically, as viewed in FIG. 3, the dental burr holders 47 are pivoted clockwise through approximately 45 degrees from the upright position to the down position.

The means employed for pivotally attaching the dental burr holders 47 to the container body 17 can take many different forms, and the construction shown in the drawings is purely illustrative. As shown in the specific embodiment, each of the dental burr holders 47 has pins 55 extending from the opposite ends thereof near the bottom wall 21, and these pins are received in corresponding holes 57 in the side walls 33 and 35.

Counterclockwise rotation of the dental burr holders 47 from the upright position is prevented by engagement between a flat inner surface 59 (FIGS. 3 and 5) of the bottom wall 21, flat bottom surfaces 61 on the dental burr holders 47 and the pin 55 and holes 57. This engagement of the bottom wall 21 and bottom surfaces 61 is shown in FIG. 5.

To enable clockwise pivotal movement of the dental burr holders 47, each of the dental burr holders has an inclined or ramp surface 63 which is inclined sufficiently to enable pivotal movement of the dental burr holders to the position of FIG. 3. Pivotal movement beyond the position of FIG. 3 is prevented by a tab 65 on the dental burr holder which cooperates with the bottom wall 21 to define the second position of the dental burr holder. Of course, means other than the tab 65 can be used for this purpose.

The dental burr holders 47 are releasably retained in the upright position by the snapping of a web 67 on each of the dental burr holders over a rib 69 projecting inwardly on the inner surface of the side wall 35. FIGS. 4 and 5 show the web 67 being releasably retained behind an associated rib 69.

Each of the dental burr holders 47 has a flange 71 which, in the upright position, is generally parallel to the bottom wall 21 and extends toward the end wall 31. In the down position of the dental burr holders 47, the flanqe 71 on one of the dental burr holders 47 cooperates with the cover 19 for holding dental burrs in the bores of the adjacent dental burr holder. This is shown by way of example in FIG. 3 where it can be seen that the flange 71 on the righthand dental burr holder 47 projects upwardly so it is in at least partial alignment with the dental burr 13 in the bore 49 of the middle dental burr holder 47. In addition, the top wall 39 of the cover 19 also blocks the dental burr 13 if it should somehow be totally misaligned with the flange 71. In this sense, the flanges 71 cooperate with the cover 19 in holding the dental burrs within the dental burr holders.

With the cover 19 removed and the dental burr holders 47 in the upright position of FIGS. 2, 4 and 5, the dental burr holders can be used to retain dental burrs in an upright position so they can be easily manually grasped and used. In addition, there is a space 73 (FIG. 2) in the compartment 25 between the lefthand dental burr holder 47 and the end wall 31 which can be used as a storage location for used dental burrs. The space 73 is provided by spacing the lefthand dental burr holder 47 farther from the end wall 31 than the righthand dental burr holder 47 is spaced from the end wall 27 (29). Of course, spaces can be provided at both ends of the compartment 25 for storage of used dental burrs, if desired.

When it is desired to clean or sterilize the used dental burr holders, they are collected from the space 73 and manually inserted into the bores 49 of the dental burr holders 47. This is done with the dental burr holders 47 in the upright position of FIG. 2. Next, the dental burr holders 47 are pivoted to the down position of FIGS. 1 and 3, and the cover 19 is attached to the container body 17 to close the open end 27 as shown in FIGS. 1 and 3. When in this position, the dimension between the outer surfaces of the top wall 39 and the bottom wall 21 is no greater than about 0.810 inch, and this dimension can be readily received within a sterilization cassette (not shown).

The receptacle 11 may then be placed within a sterilizaiton cassette, if desired, and subjected to the action of a cleaning or sterilizing fluid in the usual manner. The fluid passes through the apertures 45 and through the bores 49 to clean or sterilize, as the case may be, the burrs 13. Upon completion of this process, the cover 19 is removed, and the dental burr holders 47 are pivoted to the upright position of FIGS. 2, 4 and 5 so that the clean and/or sterile dental burrs 13 can be reused.

Although an exemplary embodiment of the invention has been shown and described, many changes, modifications and substitutions may be made by one having ordinary skill in the art without necessarily departing from the spirit and scope of this invention.

I claim:

1. A receptacle for holding dental burrs comprising:
a container including a container body and a cover;
said container body including a transverse wall and a peripheral wall joined to the transverse wall to define a compartment having an open end, said cover being positionable over the open end of the compartment;
first and second dental burr holders in said compartment, each of said dental burr holders having a plurality of bores with each of said bores terminating in an opening, each of said bores being sized and adapted to receive a dental burr through the opening thereof;
each of the dental burr holders being attached to the container body for pivotal movement between a first position in which the openings of the bores face generally outwardly of the open end of the compartment to facilitate access to any burrs in the bores and a second position in which the openings of the bores are closer to the transverse wall than in the first position;
means on said second dental burr holder cooperable with the cover for holding dental burrs in the bores of the first dental burr holder when the first and second dental burr holders are in said second position; and
said container having aperture means therein for providing access to the compartment.

2. A receptacle as defined in claim 1 wherein the dental burr holders project through the open end and out of the compartment in said first position and lie entirely within the compartment in said second position.

3. A receptacle as defined in claim 1 wherein said holding means includes a flange on the second dental burr holder.

4. A receptacle as defined in claim 1 including means on the dental burr holder for cooperating with the transverse wall to define said second position of the dental burr holder.

5. A receptacle as defined in claim 1 wherein said bores extend all the way through the dental burr holder.

6. A receptacle as defined in claim 1 wherein said aperture means includes a plurality of apertures in the cover and the transverse wall.

7. A receptacle as defined in claim 6 wherein the apertures are sufficiently small to prevent the passage of a dental burr having a diameter of 0.062 inch.

8. A receptacle as defined in claim 1 wherein the transverse wall and cover each have an outer surface and the distance between said outer surfaces with the cover positioned over the open end of the compartment is no greater than about 0.0810 inch.

9. A receptacle as defined in claim 1 including means on the container body and the first dental burr holder for restraining the first dental burr holder against pivoting out of the first position in one direction.

10. A receptacle as defined in claim 1 wherein the cover is removable from the container body.

11. A receptacle for holding dental burrs comprising:
a container including a container body and a cover;
said container body including a transverse wall and a peripheral wall joined to the transverse wall to define a compartment having an open end, said cover being positionable over the open end of the compartment;
a plurality of dental burr holders in said compartment, each of said dental burr holders having a plurality of bores with each of said bores terminating in an opening, each of said bores being sized to receive a dental burr through the opening thereof;

each of the dental burr holders being separately pivotally attached to the peripheral wall of the container body for pivotal movement between a first position in which the openings of the bores face generally outwardly of the open end of the compartment to facilitate access to any burrs in the bores and a second position in which the openings of the bores are closer to the transverse wall than in the first position;

each of the dental burr holders being separately pivotable between the first and second positions; and said container having a plurality of apertures therein providing access to the compartment even when said cover is positioned over the open end of the compartment.

12. A receptacle as defined in claim 11 wherein the peripheral wall includes opposite end walls and the dental burr holders are spaced farther from one of the end walls than from the other end wall to define a space for the storage of dental burrs.

13. A receptacle as defined in claim 11 wherein the dental burr holders are arranged in generally parallel relationship and including means on a first of said dental burr holders cooperable with the cover for holding dental burrs in the bores of an adjacent dental burr holder when said first and said adjacent dental burr holders are in said second position.

14. A receptacle as defined in claim 13 including means on each of the dental burr holders for cooperating with the transverse wall to define said second position of the dental burr holders.

15. A receptacle as defined in claim 13 wherein said bores extend all the way through the dental burr holder.

16. A method of cleaning or sterilizing dental burrs comprising:

providing a receptacle including a container body having a compartment with an open end and a cover, at least one dental burr holder in said compartment, said dental burr holder having a plurality of bores with each of said bores terminating in an opening, the dental burr holder being attached to the container body for pivotal movement between a first position in which the openings of the bores face generally outwardly of the open end of the compartment to facilitate access to any burrs in the bores and a second position in which the openings of the bores are closer to the transverse wall than in the first position;

with the dental burr holder in the first position, inserting dental burrs in the bores, respectively;

pivoting the dental burr holder to the second position;

placing the cover on the open end of the container body subsequent to said step of placing; and subjecting the dental burrs to a cleaning or sterilizing fluid through an aperture in the receptacle.

17. A receptacle for holding dental burrs comprising:

a container including a container body and a cover;

said container body including a transverse wall and a peripheral wall joined to the transverse wall to define a compartment having an open end, said cover being positionable over the open end of the compartment;

at least one dental burr holder in said compartment, said dental burr holder having a plurality of bores with each of said bores terminating in an opening, each of said bores being sized and adapted to receive a dental burr through the opening thereof;

means for pivotally attaching the dental burr holder to the container body for pivotal movement between a first position in which the openings of the bores face generally outwardly of the open end of the compartment to facilitate access to any burrs in the bores and a second position in which the openings of the bores are closer to the transverse wall than in the first position;

said container having aperture means therein for providing access to the compartment; and a tab on the dental burr holder for cooperating with the transverse wall to define said second position of the dental burr holder.

18. An assembly comprising:

a plurality of dental burs;

a container including a container body and a cover;

said container body including a transverse wall and a peripheral wall joined to the transverse wall to define a compartment having an open end, said cover being positionable over the open end of the compartment;

a plurality of dental burr holders in said compartment, said dental burr holders having a plurality of bores with each of said bores terminating in an opening, each of said bores being sized and adapted to receive a dental burr through the opening thereof, at least some of said bores having one of said dental burrs therein;

the dental burr holders being attached to the container body for pivotal movement between a first position in which the openings of the bores face generally outwardly of the open end of the compartment to facilitate access to any burrs in the bores and a second position in which the openings of the bores are closer to the transverse wall than in the first position;

said container having a plurality of apertures therein for providing access to the compartment; and said apertures being sufficiently small to prevent the passage of said dental burrs therethrough.

* * * * *

UNITED STATES PATENT AND TRADEMARK OFFICE
CERTIFICATE OF CORRECTION

PATENT NO. : 5,172,810

DATED : December 22, 1992

INVENTOR(S) : Charles A. Brewer

It is certified that error appears in the above-identified patent and that said Letters Patent is hereby corrected as shown below:

Column 5, line 14, change "flanqe" to -- flange -- .

Column 6, line 52, change "o.0810" to -- .810 -- .

Signed and Sealed this

Second Day of November, 1993

Attest:

BRUCE LEHMAN

Attesting Officer

Commissioner of Patents and Trademarks